United States Patent [19]

Malz, Jr. et al.

[11] 4,069,240

[45] Jan. 17, 1978

[54] NUCLEAR HYDROGENATION OF N-ARYL CARBAMATES

[75] Inventors: Russell E. Malz, Jr., Naugatuck; Harold Greenfield, Watertown, both of Conn.

[73] Assignee: Uniroyal, Inc., New York, N.Y.

[21] Appl. No.: 610,359

[22] Filed: Sept. 4, 1975

[51] Int. Cl.$^2$ .......................................... C07C 125/06
[52] U.S. Cl. ......................................... 560/115; 560/5
[58] Field of Search .................... 260/468 E, 468.5

[56] References Cited

U.S. PATENT DOCUMENTS

| | | | |
|---|---|---|---|
| 3,511,875 | 5/1970 | Brantley | 260/468 E |
| 3,567,764 | 3/1971 | Brantley | 260/468 E |
| 3,600,426 | 8/1971 | Grant et al. | 260/468 E |
| 3,691,234 | 9/1972 | Kiefer et al. | 260/468 E |
| 3,699,149 | 10/1972 | Yamamura et al. | 260/468 E |
| 3,867,443 | 2/1975 | Malz, Jr. et al. | 260/561 R |

OTHER PUBLICATIONS

Scopes et al., J. Chem. Soc., 1972, 2810–2811.
Weaver et al., Chem. and Ind., 4, pp. 187–188 (1973).
Weaver et al., Preprints, General Papers, Div. of Petrol. Chem., 18 (1), pp. 196–199 (1973).

*Primary Examiner*—Vivian Garner
*Attorney, Agent, or Firm*—James J. Long

[57] ABSTRACT

N-Alicyclic carbamates, useful in making polyurethanes, are prepared by nuclear hydrogenation of an N-aryl carbamate using a group VIII transition metal catalyst. E.g., dimethyl 4,4'-methylenedicarbanilate is contacted with hydrogen and ruthenium catalyst in 2-propanol medium, at 50° C. for 1.3 hours under a pressure of 500–800 psi, to form dimethyl 4,4'-methylenedicyclohexylcarbamate. Acid activation of catalyst is a feature of the invention.

18 Claims, No Drawings

NUCLEAR HYDROGENATION OF N-ARYL CARBAMATES

This invention relates to a method for the nuclear hydrogenation of N-aryl carbamates to N-alicyclic carbamates using rhodium, ruthenium, palladium, nickel, and cobalt catalysts, and to the use of an acid promoter to enhance the utility of the rhodium and the palladium catalysts and to permit the use of a platinum catalyst.

The nuclear hydrogenation of N-aryl carbamates to N-alicyclic carbamates in accordance with this invention is the key step in the most efficient route for the conversion of readily available, low cost aromatic isocyanates to non-discoloring, N-alicyclic polyurethanes. The aromatic diisocyanates are first converted to N-aryl dicarbamates by simply reacting with an alcohol, preferably methanol. The resulting N-aryl carbamate is then converted to the corresponding N-alicyclic carbamate by the method of this invention. The N-alicyclic carbamate can then be converted to valuable non-discoloring polyurethanes by transesterification reactions (transcarbamation) with an appropriate diol or mixture of diols. The conventional method for such polyurethane manufacture uses N-alicyclic isocyanates prepared from the corresponding N-alicyclic diamines by phosgenation reactions. The alicyclic dicarbamates are more efficiently and more economically prepared than the corresponding alicyclic diisocyanates, and also have the great advantage of being easily handled, chemically stable, and non-toxic.

Any N-aryl carbamate may be employed in the invention, including, for example, those of the following formulas I and II:

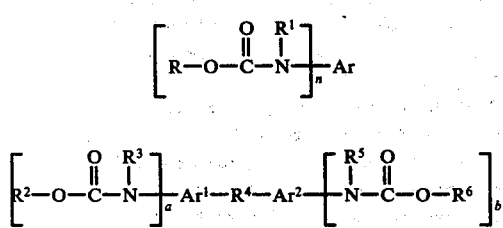

In formula I, $n$ is an integer having a value from 1 to 3, preferably 2; R is a moiety such as an alkyl group of from 1 to 18 carbon atoms, preferably 1 to 4 carbon atoms, a cycloalkyl group of from 5 to 8 carbon atoms, preferably 5 to 6 carbon atoms (such as cyclohexyl), an aryl group of from 6 to 12 carbon atoms (such as phenyl), an aralkyl or alkaryl group of from 7 to 12 carbon atoms (such as tolyl, xylyl, ethylphenyl, benzyl, phenethyl), or the like, alkyl being preferred (such as methyl, ethyl, propyl, isopropyl, n-, sec-, iso- and tert-butyl); $R^1$ is hydrogen (preferred), an alkyl group of from 1 to 8 carbon atoms (such as methyl, ethyl, propyl, isopropyl, n-, sec-, and tert-butyl), a cycloalkyl group of from 5 to 8 carbon atoms (such as cyclohexyl), or an aryl group of from 6 to 12 carbon atoms (such as phenyl); Ar is an aromatic group having a valence of $n$ and having from 6 to 18 carbon atoms, containing up to 4 fused rings, and may if desired include various substitutents such as alkyl $C_1 - C_{18}$, cycloalkyl $C_5 - C_8$, aryl $C_6 - C_{10}$ (e.g., phenyl, naphthyl), alkaryl or aralkyl $C_7 - C_{15}$, alkoxy $C_1 - C_{18}$, cycloalkoxy $C_5 - C_8$, phenoxy, benzoxy, alkanoyl $C_2 - C_{13}$, carbalkoxy $C_2 - C_{14}$, or similar substituents. Ar is frequently of phenyl, tolyl or naphthyl origin.

In formula II, $a$ and $b$ are integers having values of 1 to 2, the sum of ($a$) plus ($b$) being a whole value of from 2 to 4, preferably 2 to 3; $R^2$ and $R^6$ may be the same or different and may have the meanings stated for R in formula I above; $R^3$ and $R^5$ may be the same or different and may have the meanings stated for $R^1$ in formula I above; $R^4$ may be a single bond, —O—, $C_1 - C_8$ alkylene (such as methylene, ethylene, tetramethylene and hexamethylene), $C_5 - C_8$ cycloalkylene (such as cyclohexylene), $C_2 - C_8$ alkylidene (such as ethylidene and isopropylidene), or $C_2 - C_8$ alkenylene (such as vinylene). $Ar^1$ and $Ar^2$ may be the same or different and are di- or trivalent groups derived from radicals having the meanings assigned to Ar in formula I, especially phenylene, tolylene, xylylene and biphenylene.

Examples of aromatic carbamates useful in the invention include methyl carbanilate, isopropyl carbanilate, stearyl carbanilate, benzyl carbanilate, phenyl carbanilate, methyl 2-methylcarbanilate, methyl 3-methylcarbanilate, methyl 4-methylcarbanilate, ethyl 4-methylcarbanilate, propyl 4-methylcarbanilate, isopropyl 4-methylcarbanilate, methyl 2-ethylcarbanilate, methyl 2,3-diethylcarbanilate, methyl 2,4-diethylcarbanilate, methyl 2,5-diethylcarbanilate, methyl 2,6-diethylcarbanilate, methyl 3,4-diethylcarbanilate, methyl 3,5-diethylcarbanilate, methyl 2,4,6-trimethylcarbanilate, methyl 4-propylcarbanilate, ethyl 4-butylcarbanilate, methyl 2-biphenylcarbamate, methyl 4-biphenylcarbamate, methyl 5-indanylcarbamate, methyl 1-naphthylcarbamate, methyl 2-naphthylcarbamate, methyl 5-acenaphthenylcarbamate, ethyl 1-anthracenecarbamate, isopropyl 2-anthracenecarbamate, methyl 6-chrysenecarbamate, methyl 2-cymenecarbamate, ethyl 3-fluoranthenecarbamate, methyl 2-fluorenylcarbamate, methyl 9-phenanthrenecarbamate, isopropyl 1-pyrenecarbamate, methyl 3-methoxycarbanilate, ethyl 2-ethoxycarbanilate, methyl 4-ethoxycarbanilate, methyl 4-propoxycarbanilate, methyl 4-phenoxycarbanilate, methyl 2-methoxy-5-methylcarbanilate, methyl 4-methoxy-2-methylcarbanilate, methyl 2,4-dimethoxycarbanilate, methyl 2,5-dimethoxycarbanilate, methyl 3,5-dimethoxycarbanilate, methyl 3,4-diethoxycarbanilate, methyl 3,4,5-trimethoxycarbanilate, butyl 2,4,5-trimethoxycarbanilate, methyl 2-carbomethoxycarbanilate, methyl 3-carbomethoxycarbanilate, methyl 4-carbomethoxycarbanilate, ethyl 3-carboethoxycarbanilate, ethyl 4-carboethoxycarbanilate, methyl 4-carbophenoxycarbanilate, methyl 2-acetylcarbanilate, methyl 3-acetylcarbanilate, ethyl 4-acetylcarbanilate, methyl 1-(9-oxofluorenyl)carbamate, methyl 2-(9-oxofluorenyl)carbamate, dimethyl 1,2-benzenedicarbamate, dimethyl 1,3-benzenedicarbamate, dimethyl 1,4-benzenedicarbamate, dimethyl 2,4-toluenedicarbamate, diethyl 2,4-toluenedicarbamate, diisopropyl 2,4-toluenedicarbamate, dimethyl 2,5-toluenedicarbamate, dimethyl 2,6-toluenedicarbamate, dimethyl 3,4-toluenedicarbamate, dimethyl 4,4'-methylenedicarbanilate, diethyl 4,4'-methylenedicarbanilate, dipropyl 4,4'-methylenedicarbanilate, diisopropyl 4,4'-methylenedicarbanilate, dibutyl 4,4'-methylenedicarbanilate, distearyl 4,4'-methylenedicarbanilate, dimethyl 2,2'-biphenyldicarbamate, dimethyl 2,4'-biphenyldicarbamate, dimethyl 3,3'-biphenyldicarbamate, dimethyl 4,4'-biphenyldicarbamate, 4,4'-oxybis(methyl carbanilate), dimethyl 4,4'-diphenylethylenedicarbamate, dimethyl 4,4'-(N-methyldiphenylamine)dicarbamate, dimethyl 4,4'-(3,3'-dimethylbiphenyl)dicarbamate, dimethyl 1,2-naphthalenedicarbamate, dimethyl 1,5-naphthalenedicarbamate, diisopropyl 1,5-naphthalenedicarbamate, dimethyl 1,8-naphthalenedicarbamate, dimethyl 2,3-naphthalenedicarbamate, dimethyl 9,10-phenanthrenedicarbamate, dimethyl 4,5-acenaphthenedicarbamate, dimethyl 2,3-fluorenedicarbamate, dimethyl 2,5-fluorenedicarbamate, dimethyl 2,7-fluorenedicarbamate, dimethyl 4,5-dimethyl-1,2-benzenedicarbamate, dimethyl 4-methoxy-1,2-benzenedicarbamate, dimethyl 4-methoxy-1,3-benzenedicarbamate, dimethyl 3,3'-dimethoxy-4,4'-biphenylcarbamate, dimethyl 2,3-(9-fluorenone)dicarbamate, trimethyl 1,3,5-benzenetricarbamate, trimethyl 1,2,4-benzenetricarbamate, trimethyl 2,4,6-toluenetricarbamate, trimethyl 2,3,4-toluenetricarbamate, trimethyl 2,4,5-toluenetricarbamate, trimethyl 1,3-dimethyl-2,4,6-benzenetricarbamate, triethyl 1-ethoxy-2,4,6-benzenetricarbamate, triethyl 1-methoxy-2,4,6-benzenetricarbamate, dibutyl 1-carbophenoxy-3,5-benzenedicarbamate, diethyl 1-carbomethoxy-3,5-benzenedicarbamate, diethyl 1-carboethoxy-2,3-benzenedicarbamate, dimethyl 2,2'-benzophenonedicarbamate, dimethyl 3,3'-benzophenonedicarbamate, dimethyl 4,4'-benzophenonedicarbamate. methyl N-methylcarbanilate, ethyl N-methylcarbanilate, methyl N-ethylcarbanilate, dimethyl 4,4'-methylenedi(N-methylcarbanilate), diethyl 4,4'-methylenedi(N-methylcarbanilate), dimethyl 4,4'-methylenedi(N-ethylcarbanilate), dimethyl N,N'-dimethyl-2,4-toluenedicarbamate, dimethyl N,N'-diethyl-2,6-toluenedicarbamate, 4,4'-oxybis(methyl N-methylcarbanilate), 4,4'-oxybis (ethyl N-methylcarbanilate), 4,4'-oxybis(ethyl N-ethylcarbanilate), etc.

The catalysts employed for the nuclear hydrogenation of N-aryl carbamates in accordance with the invention are the group VIII transition metals, particularly rhodium, ruthenium, palladium, platinum, nickel and cobalt, preferably rhodium and ruthenium, and most preferably rhodium. In accordance with a preferred practice of the invention, it has been found that treatment of rhodium catalyst with an acid causes increased activity and permits extensive reuse of the catalyst, with a resulting important decrease in cost. Thus, the activity of a rhodium catalyst is markedly promoted by the addition of acid. Furthermore, repeated catalyst reuse is feasible when the spent catalyst is treated with acid. The unpredictable nature of the effect of acid is illustrated by the fact that it promotes the activity of rhodium and palladium catalysts, dramatically increases the activity of the platinum catalyst which is ordinarily inoperative in the described hydrogenation process, but actually decreases the activity of the ruthenium catalyst. In the case of a fresh catalyst, the acid treatment is most suitably accomplished in situ by adding a small amount of acid directly to the reaction mixture. For the purpose of reactivating used catalyst, the acid treatment is most conveniently effected by washing the recovered catalyst with acid prior to reuse of the catalyst. The acid may be an inorganic acid, such as sulfuric, hydrochloric, phosphoric and nitric acids, or an organic acid, such as acetic, propionic, butyric, succinic and maleic acids. For the in situ treatment of fresh catalysts, the acid may be added per se or as an appropriate solution of dilute acid, the inorganic acids being particularly suitable for this purpose. For the washing treatment of recycled catalyst, concentrated acids or dilute solutions of acid also are appropriate.

The catalysts may be prepared and used either unsupported or supported on a suitable carrier such as carbon, alumina, silica, silica-alumina, alkaline earth carbonates, kieselguhr, zeolites, pumice, clay, cellulose, asbestos, etc. They may be prepared and used as powders for slurry reactions or as pellets, spheres, or granules for fixed bed reactions.

The hydrogenation process may be carried out in the absence of any solvent medium, or preferably in the presence of an inert organic solvent, including, for example, aliphatic or cycloaliphatic alcohols, such as methyl alcohol, ethyl alcohol, n-propyl alcohol, isopropyl alcohol, n-butyl alcohol, isobutyl alcohol, sec-butyl alcohol, tert-butyl alcohol, n-amyl alcohol, isoamyl alcohol, tert-amyl alcohol, n-hexyl alcohol, cyclohexanol, n-octyl alcohol, 2-ethylhexanol, n-decyl alcohol, n-dodecanol, n-tetradecanol, n-hexadecanol, n-octadecanol, ethylene glycol, propylene glycol, glycerol etc.; ethers, such as diethyl ether, di-n-propyl ether, diisopropyl ether, methyl n-butyl ether, ethyl n-butyl ether, di-n-butyl ether, di-n-amyl ether, diisoamyl ether, di-n-hexyl ether, ethylene glycol dimethyl ether, ethylene glycol diethyl ether, ethylene glycol dibutyl ether, 1,3-dioxolane, 1,4-dioxane, tetrahydrofuran; alcohol-ethers, such as diethylene glycol, triethylene glycol, tetraethylene glycol, dipropylene glycol, 2-butoxyethanol, tetrahydrofurfuryl alcohol, etc.; esters, such as methyl acetate, ethyl acetate, propyl acetate, isopropyl acetate, butyl acetate, isobutyl acetate, methyl amyl acetate, 2-ethylhexyl acetate, diethyl succinate, etc.; nitriles, such as acetonitrile, propionitrile, butyronitrile, etc.; amides, such as formamide, acetamide, propionamide, N,N-dimethylformamide, N,N-diethylformamide, N,N-dimethylacetamide, N,N-diethylacetamide, etc.; hydrocarbons, such as n-hexane, 2-methylpentane, 3-methylpentane, 2,2-dimethylbutane, 2,3-dimethylbutane, cyclohexane, n-heptane, 3-methylhexane, n-octane, 2,2,4-trimethylpentane, 2,3,4-trimethylpentane, n-decane, decalin, etc.

The hydrogenation may be run at temperatures ranging from room temperature or below, for example, 5°, to over 200°, for example 250°, preferably 25°-200° C., or other temperatures as high as the stability of the reactants and products will permit, and at pressures ranging from atmospheric pressure or below to pressures as high as economically practical, for example, up to 10,000 psi. Preferred is a somewhat elevated pressure of, for example, 10 psi, up to, for instance, 5000 psi, usually 100 to 2500 psi. Reaction times may vary widely, ranging from a few seconds to 24 hours or longer, usually 0.1 – 15 hours. The conditions may be varied to provide an optimum economic combination of temperature, pressure, catalyst level, and cycle time for any given starting material and catalyst.

The hydrogenation reaction may be carried out in either batch or continuous systems, with either tank or pipe-line or tubular reactors, operation in a manner well known to those skilled in the art.

The following examples will serve to illustrate the practice of the invention in more detail.

HYDROGENATION OF METHYL CARBANILATE

EXAMPLE 1

A mixture of 15.1 g. (0.10 mole) of methyl carbanilate, 105 ml. of 2-propanol, and 0.60 g. of 5% Rh on carbon was added to a 300-ml. Magne Drive (tradmark)

autoclave. The vessel was sealed, purged first with nitrogen and then with hydrogen, and pressured with hydrogen to 600 psig. The autoclave was heated with agitation at 500–800 psig for 0.3 hr. at 25°–75°, followed by an additional 0.8 hr. at 75° with little or no gas absorption. The autoclave was cooled and depressurized. The reaction product was removed and filtered through Celite (trademark) filter aid to remove the catalyst. The solvent was removed in a rotary evaporator under vacuum. The white solid residue was dried in a vacuum dessicator and consisted of 15.1 g. (96% yield) of methyl cyclohexylcarbamate, m.p. 73°–74°. An authentic sample prepared from cyclohexyl isocyanate and methanol melted at 73.5°–74°.

The examples in Table I illustrate the use of several catalysts for the nuclear hydrogenation of methyl carbanilate to methyl cyclohexylcarbamate. Rhodium is considerably more active than the other catalysts, and platinum shows no apparent activity.

TABLE I

Hydrogenation of Methyl Carbanilate[a]

| Example No. | Catalyst[b] Metal | wt., g. | conc., g./l | Temp., °C | Pressure, psig. | Time, hr. | Yield methyl cyclohexylcarbamate, mole % |
|---|---|---|---|---|---|---|---|
| 1 | Rh | 0.60 | 5 | 25–75 | 500–800 | 0.3 | 96 |
| 2 | Ru | 2.4 | 20 | 75 | 500–800 | 0.8 | 95 |
| 3 | Pd | 2.4 | 20 | 100 | 620–680 | 2.8 | 22[c] |
| 4 | Pd | 2.4 | 20 | 125 | 500–800 | 13 | 47[c] |
| 5 | Pt | 2.4 | 20 | 160 | 850 | 1.8 | 0[d] |
| 6 | Ni | 2.4 | 20 | 150 | 660–880 | 12.5 | 30[c] |
| 7 | Co | 2.4 | 20 | 150 | 500–900 | 14.5 | 45[c] |

[a]Each experiment was run in a 300-ml., stainless-steel Magne Drive autoclave with 15.1 g. (0.10 mole) of methyl carbanilate and 105 ml. of 2-propanol.
[b]The Rh, Ru, Pd and Pt catalysts were 5% metal on carbon. The Ni and Co catalysts were 50% metal on kieselguhr; the weight of the catalyst is given as the weight of the metal plus support, in this and in subsequent tables.
[c]Determined by infrared analysis of residue product.
[d]No detectable reaction.

The effect of acid on the rate of hydrogenation of methyl carbanilate is shown in Table II. Traces of acid promote the rhodium, palladium, and platinum catalysts, but inhibit the ruthenium catalyst. The acid promotion is presumably due to the neutralization of traces of bases initially present and/or formed from the carbamate. The effect with rhodium is more pronounced at lower catalyst levels, when the catalyst is more susceptible to poisoning, and at higher temperatures, when larger amount of amine impurities would be expected (examples 10–12).

The effect of acid on platinum is dramatic and even permits reuse of the platinum catalyst (example 20).

The effect of acid on ruthenium seems to be the result of two opposing factors, an acid inhibition of the catalyst and the neutralization of basic inhibitors. The latter effect appears to increase in importance when lower catalyst levels produce longer reaction times that permit greater amine formation (examples 15 and 16).

Table II

Effect of Acid in Hydrogenation of Methyl Carbanilate[a]

| Example No. | Catalyst Metal | wt., g. | conc., g./l | Acid present [b] | Temp. °C | Pressure, psig. | Time for complete conversion, hr. |
|---|---|---|---|---|---|---|---|
| 8 | Rh | 0.20 | 1.7 | no | 45 | 500–800 | 4.0 |
| 9 | Rh | 0.20 | 1.7 | yes | 45 | 500–800 | 3.5 |
| 10 | Rh | 0.10 | 0.83 | no | 100 | 500–800 | 2.2 |
| 11 | Rh | 0.10 | 0.83 | yes | 100 | 500–800 | 0.9 |
| 12 | Rh | 0.10 | 0.83 | yes[c] | 100 | 500–800 | 1.7 |
| 13 | Ru | 2.4 | 20 | no | 80 | 500–800 | 0.7 |
| 14 | Ru | 2.4 | 20 | yes | 80 | 500–800 | 2.7 |
| 15 | Ru | 0.60 | 5 | no | 90 | 500–800 | 9.0 |
| 16 | Ru | 0.60 | 5 | yes | 90 | 500–800 | 9.5 |
| 3 | Pd | 2.4 | 20 | no | 100 | 620–680 | 2.8 (22% conversion) |
| 17 | Pd | 2.4 | 20 | yes | 100 | 500–800 | 2.2 |
| 5 | Pt | 2.4 | 20 | no | 160 | 850 | no conversion |
| 18 | Pt | 2.4 | 20 | yes | 45 | 500–800 | 4.0 |
| 19 | Pt | 0.8 | 6.7 | yes | 75 | 500–800 | 5.0 |
| 20 | Pt | d | d | yes | 75 | 500–800 | 8.8 |

[a]Each experiment was run in a 300-ml., stainless-steel, Magne Drive autoclave with 15.1 g. (0.10 mole) of methyl carbanilate and 105 ml. of 2-propanol.
[b]0.10 ml. (ca. 6 × $10^{-4}$ equiv.) of 6N sulfuric acid.
[c]0.10 ml. (ca. 6 × $10^{-4}$ equiv.) of 6N acetic acid.
[d]Used catalyst recovered from example 19.

HYDROGENATION OF CYCLOHEXYL CARBANILATE

EXAMPLE 21

A mixture of 21.9 g. (0.10 mole) of cyclohexyl carbanilate, 77 ml. of 2-propanol, and 3.0 g. of 5% on carbon was added to a 0.5-l., glass, low pressure, Parr (trademark) shaker bottle. The apparatus was assembled, purged first with nitrogen and then with hydrogen, and pressured with hydrogen to 50 psig. The reaction mixture was agitated at room temperature and 50 to 25 psig for 3.0 hr., followed by an additional 0.8 hr. with little or no gas absorption. The reaction product was filtered through Celite filter aid to remove the catalyst. The solvent was removed in a rotary evaporator under vacuum. The solid residue consisted of 22.3 g. (99% yield) of cyclohexyl cyclohexylcarbamate, m.p. 77°–78°. Anal. Calcd. for $C_{13}H_{23}NO_2$: C, 69.29; H, 10.30; N, 6.21. Found: C, 69.43; H, 10.10; N, 6.20.

EXAMPLE 22

A mixture of 21.9 g. (0.10 mole) of cyclohexyl carbanilate, 100 ml. of 2-propanol, and 2.4 g. of 5% Rh on carbon was added to a 300-ml. Magne Drive autoclave. The vessel was sealed, purged first with nitrogen and then with hydrogen, and pressured with hydrogen to 700 psig. The autoclave was agitated at 25° and 500–800 psig for 0.4 hr., followed by an additional 0.9 hr. with little or no gas absorption. The autoclave was cooled and depressurized. The reaction product was removed and filtered through Celite filter aid to remove the catalyst. The solvent was removed in a rotary evaporator under vacuum. The white solid residue consisted of 21.9 g. (97% yield) of cyclohexyl cyclohexylcarbamate, m.p. 77°–78°.

HYDROGENATION OF METHYL 1-NAPHTHYLCARBAMATE

EXAMPLE 23

A mixture of 20.1 g. (0.10 mole) of methyl 1-naphthylcarbamate, 100 ml. of 2-propanol, and 2.4 g. of 5% Rh on carbon was added to a 300-ml. Magne Drive autoclave. The vessel was sealed, purged first with nitrogen and then with hydrogen, and pressured with hydrogen to 600 psig. The autoclave was agitated at 22°–31° and 500–800 psig for 3.7 hr., followed by an additional 0.8 hr. with little or no gas absorption. The autoclave was cooled and depressurized. The reaction product was removed and filtered through Celite filter aid to remove the catalyst. The solvent was removed in a rotary evaporator under vacuum. The solid residue consisted of 21.0 g. (99.5% yield) of a mixture of isomeric methyl 1-decahydronaphthylcarbamates, m.p. 104°–114°. Anal. Calcd. for $C_{12}H_{21}NO_2$: C, 68.20; H, 10.03; N, 6.63. Found: C, 68.61; H, 9.71; N, 6.69.

HYDROGENATION OF DIMETHYL 4,4′-METHYLENEDICARBANILATE

A. Effect of purity of the dimethyl 4,4′-methylenedicarbanilate on the Rh-catalyzed hydrogenation Table III illustrates how the purity of the N-aryl carbamate, in this case 4,4′-methylenedicarbanilate, greatly effects its rate of rhodium-catalyzed hydrogenation. Attempted hydrogenations of dimethyl 4,4′-methylenedicarbanilate that had been prepared under non-anhydrous conditions always resulted in catalyst poisoning and poor conversions.

Table III

Effect of Purity of Dimethyl 4,4′-Methylenedicarbanilate on Rate of Rh-Catalyzed Hydrogenation to Dimethyl 4,4′-Methylenedicyclohexylcarbamate[a]

| Example No. | Source of Starting Material[b] | Catalyst wt., g. | conc., g./l. | Temp., °C. | Time for complete conversion, hr. |
|---|---|---|---|---|---|
| 24 | I | 2.4 | 20 | 50 | 6.5 |
| 25 | II | 2.4 | 20 | 50 | 1.3 |
| 26 | I | 0.8 | 6.7 | 100 | 5.3 (69% conversion) |
| 27 | II | 0.8 | 6.7 | 100 | 0.7 |
| 28 | II | 0.6 | 5 | 75 | 6.0 |
| 29 | III | 0.6 | 5 | 75 | 3.0 |

[a]Each experiment was run in a 300-ml., stainless-steel, Magne Drive autoclave with 20.0 g. (0.064 mole) of dimethyl 4,4′-methylenedicarbanilate, 100 ml. of 2-propanol, and a 5% Rh on carbon catalyst at 500–800 psig.
[b]Each batch was prepared under anhydrous conditions from methanol and methylenebis(p-phenylisocyanate). I was prepared from practical grade methylenebis(p-phenylisocyanate). II was preapred from high purity methylene-p-phenyl diisocyanate. III was prepared by recrystallization of II from methanol.

B. Effect of temperature and catalyst level interaction on rate of Rh-catalyzed hydrogenation of dimethyl 4,4′-methylenedicarbanilate Table IV illustrates the interrelated effects of catalyst level and temperature on reaction rate and catalyst inhibition in the rhodium-catalyzed hydrogenation of dimethyl 4,4′-methylenedicarbanilate. At the lower catalyst level (examples 30–32), catalyst poisoning produces a decrease in conversion in going from 75° to 100°, and, in spite of a very rapid initial rate of hydrogenation, even more severe poisoning and lower conversion at 150°. At the higher catalyst level (examples 33, 34 and 27), the catalyst poisoning is less pronounced because of the larger number of active sites, and the hydrogenation rate increases with increasing temperature in the lower range of 50° to 100°. The obvious explanation is that higher temperatures result in greater rates of nuclear hydrogenation, but also produce increasing quantities of by-products that poison the catalyst. The severity of poisoning will be inversely related to the amount of catalyst present.

Table IV

Relationship of Catalyst Level and Temperature in Rh-Catalyzed Hydrogenation of Dimethyl 4,4′-Methylenedicarbanilate[a]

| Example No. | Catalyst wt., g. | conc., g./l. | Temp., °C. | Time for complete conversion, hr. |
|---|---|---|---|---|
| 30 | 0.4 | 3.3 | 75 | 13 |
| 31 | 0.4 | 3.3 | 100 | 6.0 (65% conversion)[b] |
| 32 | 0.4 | 3.3 | 150 | 0.3 (50% conversion)[c] |
| 33 | 0.8 | 6.7 | 50 | 12 |
| 34 | 0.8 | 6.7 | 75 | 3.0 |
| 27 | 0.8 | 6.7 | 100 | 0.7 |

[a]Each experiment was run in a 300-ml., stainless-steel, Magne Drive autoclave with 20.0 g. (0.064 mole) of dimethyl 4,4′-methylenedicarbanilate, 100 ml. of 2-propanol, and a 5% Rh on carbon catalyst at 500–800 psig.
[b]Reaction going very slowly when shut down.
[c]Reaction had stopped.

A detailed description of example 34 follows:

A mixture of 20.0 g. (0.064 mole) of dimethyl 4,4′-methylenedicarbanilate (batch II), 100 ml. of 2-propanol, and 0.8 g. of 5% Rh on carbon was added to a 300-ml. Magne Drive autoclave. The vessel was sealed, purged first with nitrogen and then with hydrogen, and pressured with hydrogen to 600 psig. The autoclave was agitated at 75° and 500–800 psig for 3.0 hr., followed by an additional 0.8 hr. with little or no gas absorption. The gas absorption was aproximately quantitative. The autoclave was cooled and depressurized. The reaction product was removed and the catalyst separated from the reaction mixture by centrifugation, and then washed successively with three 600-ml. portions of methanol, one 300-ml. portion of 2-propanol, and one 150-ml. portion of 2-propanol. The solvent was removed from the reaction product in a rotary evaporator under vacuum. The white solid residue was dried in a vacuum dessicator and consisted of 20.4 g. (98% yield) of a mixture of isomers of dimethyl 4,4′-methylenedicyclohexylcarbamate, m.p. 128°–135°. Anal. Calcd. for $C_{17}H_{30}N_2O_4$: C, 62.56; H, 9.25; N, 8.58. Found: C, 63.10; H, 9.26; N, 8.35.

C. Acid-activation of hydrogenation of dimethyl 4,4′-methylenedicarbanilate

The promotion by acid of the rhodium-, palladium-, and platinum-catalyzed hydrogenation of dimethyl 4,4′-methylenedicarbanilate is shown in Table V. The results are similar to those obtained in the hydrogenation of methyl carbanilate (Table II). Again, rhodium is by far the most active catalyst.

Table V

Acid Promotion in the Hydrogenation of Dimethyl 4,4'-Methylenedicarbanilate[a]

| Example No. | Catalyst Metal | wt., g. | conc., g./l. | Acid present[b] | Temp., °C. | Pressure, psig | Time for complete conversion, hr. |
|---|---|---|---|---|---|---|---|
| 34 | Rh | 0.8 | 6.7 | none | 75 | 500–800 | 3.0 |
| 35 | Rh | 0.8 | 6.7 | sulfuric | 75 | 500–800 | 0.8 |
| 36 | Rh | 0.8 | 6.7 | hydrochloric | 75 | 500–800 | 1.8 |
| 37 | Rh | 0.8 | 6.7 | phosphoric | 75 | 500–800 | 1.4 |
| 29 | Rh | 0.6 | 5 | none | 75 | 500–800 | 3.0 |
| 38 | Rh | 0.6 | 5 | sulfuric | 75 | 500–800 | 1.0 |
| 39 | Rh | 0.6 | 5 | sulfuric[c] | 75 | 500–800 | 0.8 |
| 40 | Pd | 2.4 | 20 | none | 100 | 1120–1155 | 5.0 (16% conversion) |
| 41 | Pd | 2.4 | 20 | sulfuric | 100 | 900–1200 | 5.0 (34% conversion) |
| 42 | Pt | 2.4 | 20 | none | 125 | 725 | no conversion |
| 43 | Pt | 2.4 | 20 | sulfuric | 85 | 500–800 | 5.6 (82% conversion) |

[a]Each experiment was run in a 300-ml., stainless-steel, Magne-Drive autoclave with 20.0 g. (0.064 mole) of dimethyl 4,4'-methylenedicarbanilate, 100 ml. of 2-propanol, and a 5% metal on carbon catalyst.
[b]0.10 ml. (ca. 6 × 10$^{-4}$ equiv.) of acid used.
[c]0.50 ml. (ca. 30 × 10$^{-4}$ equiv.).

D. Catalyst reuse in Rh-catalyzed hydrogenation of dimethyl 4,4'-methylenedicarbanilate Table VI illustrates how the rhodium catalyst recovered from the hydrogenation of dimethyl 4,4'-methylenedicarbanilate retains sufficient activity to permit several reuses. Furthermore, examples 48 and 49 illustrate how extremely efficient an acid wash is in restoring the activity of the used catalyst. Part of the enhanced activity in these experiments may be the result of acid promotion (see Tables II and V) by traces of acid remaining on the catalyst from the acid wash.

Table VI

Catalyst Reuse in Rh-Catalyzed Hydrogenation of Dimethyl 4,4'-Methylenedicarbanilate[a]

| Example No. | Catalyst | Catalyst treatment | Time for complete conversion, hr. |
|---|---|---|---|
| 34 | 0.8 g. (6.7 g./l.) fresh | none | 3.0 |
| 44 | recovered from example 34 | b | 4.0 |
| 45 | recovered from example 44 | b | 5.0 |
| 46 | recovered from example 45 | b | 8.4 |
| 28 | 0.6 g. (5.0 g./l.) fresh | none | 6.0 |
| 47 | recovered from example 28 | b | 9.0 |
| 48 | recovered from example 47 | c | 4.3 |
| 49 | recovered from example 48 | c | 6.0 |

[a]Each experiment was run in a 300-ml., stainless-steel, Magne Drive autoclave with 20.0 g. (0.064 mole) of dimethyl 4,4'-methylenedicarbanilate, 100 ml. of 2-propanol and a 5% Rh on carbon catalyst at 75° and 500–800 psig.
[b]Washed successively with methanol and 2-propanol.
[c]Washed successively with methanol, 6N sulfuric acid, and 2-propanol.

Table VII shows the feasibility of catalyst reuse in the rhodium-catalyzed hydrogenation of dimethyl 4,4'-methylenedicarbanilate with acid promotion, both with and without an acid wash of the recovered catalyst.

Table VII

Catalyst Reuse in Acid-Promoted Rh-Catalyzed Hydrogenation of Dimethyl 4,4'-Methylenedicarbanilate[a]

| Example No. | Catalyst | Catalyst treatment | Promoting Acid | Time for complete conversion, hr. |
|---|---|---|---|---|
| 35 | 0.8 g. (6.7 g./l.) fresh | None | Sulfuric | 0.8 |
| 50 | recovered from example 35 | b | Sulfuric | 1.8 |
| 37 | 0.8 g. (6.7 g./l.) fresh | None | Phosphoric | 1.4 |
| 51 | recovered from example 37 | c | Phosphoric | 1.8 |

[a]Each experiment was run in a 300-ml., stainless-steel, Magne Drive autoclave with 20.0 g. (0.064 mole) of dimethyl 4,4'-methylenedicarbanilate, 100 ml. of 2-propanol, a 5% Rh on carbon catalyst, and 0.10 ml. (ca. 6 × 10$^{-4}$ equiv.) of either 6N sulfuric acid or 6N phosphoric acid at 75° and 500–800 psig.
[b]Washed successively with methanol and 2-propanol.
[c]Washed successively with methanol, 6N sulfuric acid, and 2-propanol.

HYDROGENATION OF DIISOPROPYL 4,4'-METHYLENEDICARBANILATE

EXAMPLE 52

A mixture of 23.6 g. (0.064 mole) of diisopropyl 4,4'-methylenedicarbanilate, 97 ml. of 2-propanol, and 2.4 g. of 5% Rh on carbon was added to a 300-ml. Magne Drive autoclave. The vessel was sealed, purged first with nitrogen and then with hydrogen, and pressured with hydrogen to 600 psig. The autoclave was agitated at 40° and 500–800 psig for 7.6 hr., followed by an additional 1.1 hr. with little or no gas absorption. The autoclave was cooled and depressurized. The reaction product was removed and filtered through Celite filter aid to remove the catalyst. The solvent was removed on a rotary evaporator under vacuum. The solid residue consisted of 20.2 g. (83% yield) of a mixture of isomeric diisopropyl 4,4'-methylenedicyclohexylcarbamates, m.p. 182°–206°, Anal. Calcd. $C_{21}H_{38}N_2O_4$: C, 65.93; H, 10.01; N, 7.32. Found: C, 66.39; H, 10.24; N, 7.48.

EXAMPLE 53

Example 52 was repeated at 75° for 6.0 hr. Approximately the theoretical gas absorption took place in 3.0 hr., with most of the reaction completed below reaction temperature, followed by a slow gas absorption for 3.0 hr. at 75° and little or no absorption in the last 3.0 hr. at 75°.

HYDROGENATION OF DIMETHYL TOLUENEDICARBAMATE

EXAMPLE 54

A mixture of 23.8 g. (0.10 mole) of dimethyl toluenedicarbamates (prepared from the 80:20 mixture of 2,4- and 2,6-toluene diisocyanates), 100 ml. of 2-propanol and 2.4 g. of 5% Rh on carbon was added to a 300-ml. Magne Drive autoclave. The vessel was sealed, purged first with nitrogen and then with hydrogen, and pressured with hydrogen to 600 psig. The autoclave was agitated at room temperature and 500–800 psig for 2.8 hr., with little or no gas absorption in an additional 0.8 hr. The autoclave was depressurized and the reaction product removed and filtered through Celite filter aid to remove the catalyst. The solvent was removed on a rotary evaporator under vacuum. The solid white residue consisted of 24.9 g. (102% yield) of a mixture of isomeric dimethyl methylcyclohexyldicarbamates, m.p. 165°–189°. Anal. Calcd. for $C_{11}H_{20}N_2O_4$: C, 54.07; H, 8.27; N, 11.46. Found: C, 54.24; H, 8.23; N, 11.44.

HYDROGENATION OF DIMETHYL 1,5-NAPHTHALENEDICARBAMATE

EXAMPLE 55

A mixture of 15.1 g. (0.055 mole) of dimethyl 1,5-naphthalenedicarbamate, 105 ml. of 2-propanol, and 2.4 g. of 5% Rh on carbon was added to a 300-ml. Magne Drive autoclave. The vessel was sealed, purged first with nitrogen and then with hydrogen, and pressured with hydrogen to 600 psig. The autoclave was agitated at 45° and 500–800 psig for 3.8 hr., with little or no gas absorption in an additional 1.3 hr. The reaction product was removed and filtered through Celite filter aid to remove the catalyst. The solvent was removed on a rotary evaporator under vacuum. The solid white residue consisted of 14.2 g. (91% yield) of a mixture of isomeric dimethyl 1,5-decahydronaphthalenedicarbamates, m.p. 211°–233°. Anal. Calcd. for $C_{14}H_{24}N_2O_4$: C, 59.14; H, 8.51; N, 9.85. Found: C, 59.20; H, 8.57; N, 9.79.

HYDROGENATION OF ETHYL N-METHYLCARBANILATE

EXAMPLE 56

A mixture of 17.9 g. (0.10 mole) of ethyl N-methylcarbanilate, 100 ml. of 2-propanol, and 2.4 g. of 5% Rh on carbon was added to a 300 ml. Magne Drive autoclave. The vessel was sealed, purged first with nitrogen and then with hydrogen, and pressured with hydrogen to 600 psig. The autoclave was agitated at 30°–40° and 500–800 psig for 0.3 hr., when gas absorption stopped. The reaction product was removed and filtered through Celite filter aid to remove the catalyst. Most of the solvent was removed on a rotary evaporator under vacuum. Distillation gave a quantitative yield of ethyl N-methylcyclohexylcarbamate, b.p. 78°–82° at 2 mm., mostly 81°–2° at 2 mm. An elemental analysis was obtained on a middle cut from the distillation. Anal. Calcd. for $C_{10}H_{19}O_2N$: C, 64.83; H, 10.34; N, 7.56. Found: C, 64.73; H, 10.32; N, 7.44.

HYDROGENATION OF DIETHYL 4,4'-METHYLENEDI(N-METHYLCARBANILATE)

EXAMPLE 57

A mixture of 29.5 g. (0.0796 mole) of diethyl 4,4'-methylenedi(N-methylcarbanilate), prepared by the reaction of 4,4'-methylenebis (N-methylaniline) with ethyl chloroformate in benzene in the presence of calcium carbonate, 90 ml. of 2-propanol, and 2.4 g. of 5% Rh on carbon was added to a 300 ml. Magne Drive autoclave. The vessel was sealed, purged first with nitrogen and then with hydrogen, and pressured with hydrogen to 600 psig. The autoclave was agitated at 425–800 psig. for 7 hr. at 50° followed by 13 hr. at 75°, with little or no gas absorption in the last 2 hr. The hydrogen absorption was approximately quantitative. The reaction product was removed and filtered through Celite filter aid to remove the catalyst. The solvent was removed on a rotary evaporator. After drying in a vacuum dessicator over Drierite, the viscous liquid residue consisted of 29.5 g. (97% yield) of a mixture of isomers of diethyl 4,4'-methylenedi(N-methylcyclohexylcarbamate). Anal. Calcd. for $C_{21}H_{38}N_2O_4$: C, 65.94; H, 10.01; N, 7.32. Found: C, 66.26; H, 10.06; N, 7.41.

We claim:

1. A method of making an N-alicyclic carbamate comprising contacting an N-aryl carbamate with hydrogen in an inert solvent medium in the presence of a metal hydrogenation catalyst selected from the group consisting of rhodium, acid-treated rhodium, ruthenium, palladium, acid-treated palladium, nickel, cobalt and acid-treated platinum catalyst, whereby nuclear hydrogenation of the said N-aryl carbamate takes place to form the said N-alicyclic carbamate, the said N-aryl carbamate being selected from the group consisting of those of the formulas I and II as follows:

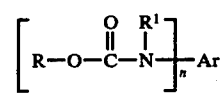

I

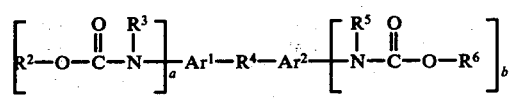

II wherein, in formula I: $n$ is an integer having a value from 1 to 3; R is alkyl having from 1 to 18 carbon atoms, a cycloalkyl group having from 5 to 8 carbon atoms, an aryl group having from 6 to 12 carbon atoms, an aralkyl or alkaryl group having from 7 to 12 carbon atoms; $R^1$ is hydrogen, an alkyl group having from 1 to 8 carbon atoms, a cycloalkyl group having from 5 to 8 carbon atoms, or an aryl group having from 6 to 12 carbon atoms; and Ar is an aryl group having a valence of $n$ and having from 6 to 18 carbon atoms, containing up to 4 fused rings;

and wherein, in formula II: $a$ and $b$ are integers having values of 1 or 2; $R^2$ and $R^6$ are the same or different and have meanings stated for R in formula I; $R^3$ and $R^5$ are the same or different and have meanings stated for $R^1$ in formula I; $R^4$ is a single bond, —O—, $C_1$–$C_8$ alkylene, $C_5$–$C_8$ cycloalkylene, $C_2$–$C_8$ alkylidene, or $C_2$–$C_8$ alkenylene; and $Ar^1$ and $Ar^2$ are the same or different and are divalent or trivalent groups derived from radicals having the meanings assigned to Ar in formula I;

the said method being carried out at a temperature of 25°–200° C and a pressure of 100 to 2500 psi.

2. A method as in claim 1 in which the said hydrogenation catalyst is rhodium or ruthenium catalyst.

3. A method as in claim 1 in which the said hydrogenation catalyst is rhodium catalyst.

4. A method as in claim 1 in which the said hydrogenation catalyst is acid-treated rhodium, acid-treated palladium, or acid-treated platinum catalyst.

5. A method as in claim 1 in which the said hydrogenation catalyst is acid-treated rhodium catalyst.

6. A method as in claim 5 in which the starting N-aryl carbamate is methyl carbanilate and the resulting N-alicyclic carbamate product is methyl cyclohexylcarbamate.

7. A method as in claim 5 in which the starting N-aryl carbamate is cyclohexyl carbanilate and the resulting N-alicyclic carbamate product is cyclohexyl cyclohexylcarbamate.

8. A method as in claim 1 in which the starting N-aryl carbamate is methyl 1-naphthylcarbamate and the resulting N-alicyclic carbamate product is a mixture of isomeric methyl 1-decahydronaphthylcarbamates.

9. A method as in claim 5 in which the starting N-aryl carbamate is ethyl N-methylcarbanilate and the resulting N-alicyclic carbamate product is ethyl N-methylcyclohexylcarbamate.

10. A method as in claim 5 in which the starting N-aryl carbamate is diethyl 4,4′-methylenedi(N-methylcarbanilate) and the resulting N-alicyclic carbamate product is a mixture of isomers of diethyl 4,4′-methylenedi(N-methylcyclohexylcarbamate).

11. A method as in claim 1 in which $n$ is 2, R is an alkyl group having from 1 to 4 carbon atoms, a cycloalkyl group having 5 to 6 carbon atoms, phenyl, tolyl, xylyl, ethylphenyl, benzyl, or phenethyl, $R^1$ is hydrogen, Ar is phenylene, tolylene or naphthylene, $R^2$ and $R^6$ have meanings stated herein for R; $R^3$ and $R^5$ have meanings stated herein for $R^1$; and $Ar^1$ and $Ar^2$ are phenylene, tolylene, xylylene or biphenylene.

12. A method as in claim 11 in which the inert organic solvent is an aliphatic alcohol.

13. A method as in claim 11 in which the hydrogenation catalyst is rhodium catalyst, with or without acid treatment.

14. A method as in claim 13 in which the catalyst is acid-treated.

15. A method as in claim 13 in which the starting N-aryl carbamate is dimethyl 4,4′-methylenedicarbanilate and the resulting N-alicyclic carbamate product is a mixture of isomers of dimethyl 4,4′-methylenedicyclohexylcarbamate.

16. A method as in claim 13 in which the starting N-aryl carbamate is diisopropyl 4,4′-methylenedicarbanilate and the resulting N-alicyclic carbamate product is a mixture of isomers of diisopropyl 4,4′-methylenedicyclohexylcarbamate.

17. A method as in claim 13 in which the starting N-aryl carbamate is dimethyl toluenedicarbamate and the resulting N-alicyclic carbamate is a mixture of isomers of dimethyl methylcyclohexyldicarbamate.

18. A method as in claim 13 in which the starting N-aryl carbamate is dimethyl 1,5-naphthalenedicarbamate and the resulting N-alicyclic carbamate product is a mixture of isomers of dimethyl 1,5-decahydronaphthalenedicarbamate.

* * * * *